United States Patent [19]

Land

[11] Patent Number: 5,067,749

[45] Date of Patent: Nov. 26, 1991

[54] METHOD AND APPARATUS FOR OBTAINING AND RECORDING FINGERPRINT INDICIA

[76] Inventor: Larry D. Land, 1946 Edgerton, St. Paul, Minn. 55117

[21] Appl. No.: 294,219

[22] Filed: Jan. 9, 1989

[51] Int. Cl.$^5$ ............................................. B42D 15/00
[52] U.S. Cl. .................................... 283/117; 283/68; 283/69
[58] Field of Search .................... 283/115, 74, 68, 69, 283/70, 78, 75, 117; 479/1

[56] References Cited

U.S. PATENT DOCUMENTS 3,408,217  6/1965  Obuchi .................................. 283/68
4,669,753  6/1987  Land et al. ............................ 283/68

Primary Examiner—Paul A. Bell
Attorney, Agent, or Firm—Douglas L. Tschida

[57] ABSTRACT

A method and apparatus for recording prints of digital extremities, and the like, utilizes a transparent print indicia recording medium to record images corresponding to the digits of an individual wherein the record, thus obtained, on the adhesive coated surface of the transparent medium may be sealed to a transparent base and then utilized to generate a plurality of image displaying records which may be easily disseminated and used by others in various postures and manners, e.g., front or back observation of a digit indicia as well as transporation or communication of reproductions of the original records to remote locations and/or storage in typical memory devices such as magnetic tape or the like.

14 Claims, 14 Drawing Sheets

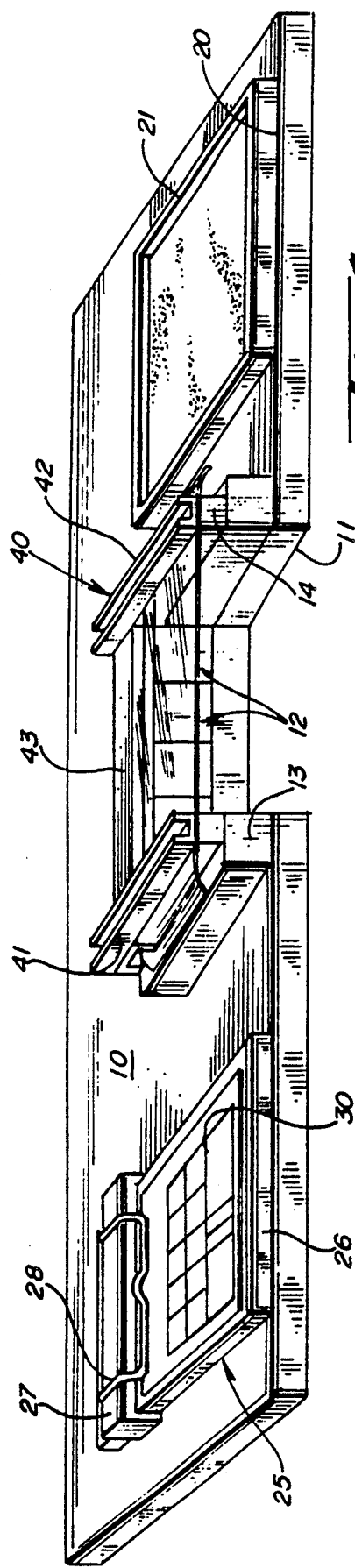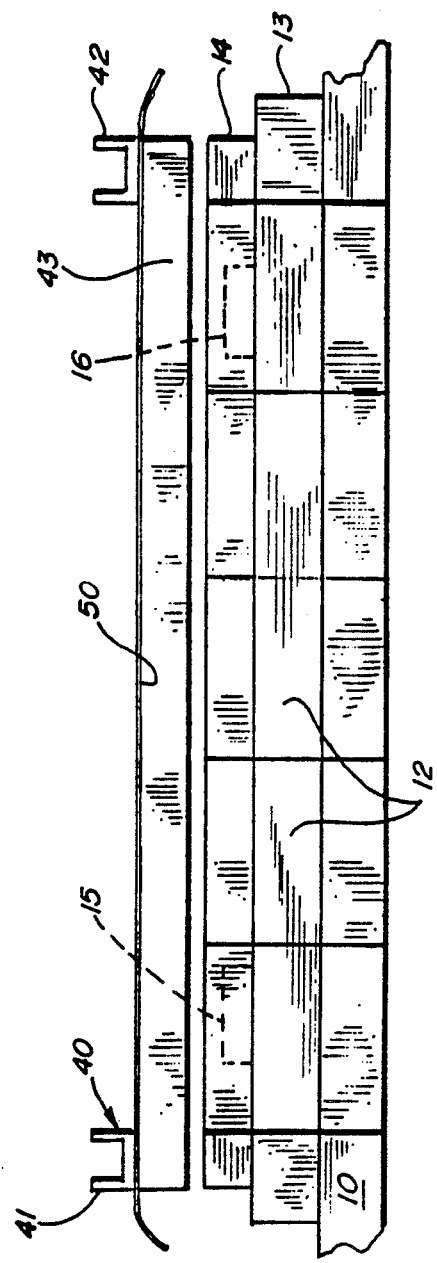

FIG. 10

STATE OF MINNESOTA
BUREAU OF CRIMINAL APPREHENSION

| DATE | LAST NAME | FIRST NAME | MIDDLE NAME |
|------|-----------|------------|-------------|

PAT. #4689753

| 1. R. THUMB | 2. R. INDEX | 3. R. MIDDLE | 4. R. RING | 5. R. LITTLE |
|---|---|---|---|---|
| 6. L. THUMB | 7. L. INDEX | 8. L. MIDDLE | 9. L. RING | 10. L. LITTLE |
| LEFT FOUR FINGERS SIMULTANEOUSLY | | L. THUMB | R. THUMB | RIGHT FOUR FINGERS SIMULTANEOUSLY |

STATE OF MINNESOTA
BUREAU OF CRIMINAL APPREHENSION

| DATE | LAST NAME | FIRST NAME | MIDDLE NAME |
|---|---|---|---|

PAT. #4689753

| 1. R. THUMB | 2. R. INDEX | 3. R. MIDDLE | 4. R. RING | 5. R. LITTLE |
|---|---|---|---|---|
| 6. L. THUMB | 7. L. INDEX | 8. L. MIDDLE | 9. L. RING | 10. L. LITTLE |

| LEFT FOUR FINGERS SIMULTANEOUSLY | L. THUMB | R. THUMB | RIGHT FOUR FINGERS SIMULTANEOUSLY |
|---|---|---|---|

METHOD AND APPARATUS FOR OBTAINING AND RECORDING FINGERPRINT INDICIA

FIELD OF THE INVENTION

1. Background of the Invention

This invention relates generally to the field of obtaining and recording images of the digital extremities of an individual and is more particularly directed toward a method and apparatus for obtaining, recording, and further processing of such digital image information.

2. Prior Art

The subject matter of this application is an improvement on my U.S. Pat. No. 4,669,753 and the earlier U.S. Patents. cited and noted therein, none of which are believed to constitute relevant prior art above and beyond that shown, described and claimed is my own patent.

In the further development of my digital image records keeping system, known as the Land System, a method and apparatus has been developed which further facilitates the obtaining of images of the digital extremities of an individual in an orderly, efficient and more accurate manner and provides such recorded information in a form which may be easily transmitted or communicated to improved records keeping devices as well as to remote locations as, for example, by wireless or wired communications systems.

SUMMARY OF THE INVENTION

The object of my invention is to provide an improved method and apparatus for obtaining and recording the images of the digital extremities of an individual.

A further object of my invention is to provide an image recording apparatus and method which may be used under difficult circumstances, such as recording the images of the digital extremities of an uncooperative immovable body, such as a corpse. A still further object of my invention is to provide a permanent record of images of the digital extremities of an individual on a medium which may be used to create further records in the form of copies disposed on transparent and or opaque recording medium and which may be readily transmitted over long distances from magnetic memories or the like.

In one embodiment of apparatus involving the principles of my invention, an open-sided frame is provided to accept and hold a length of substantially inextensible, flexible plastic tape which is provided with an adhesive coating on one major surface and which is intended to receive impressions from the digital extremities of an individual to record the patterns existing thereon for storage and further processing. Once the impressions, or records, are disposed in or on the adhesive coating on the tape, which may be applied about and around the extremity of a digit, the images may be permanently disposed upon a transparent carrier therefor or may be scanned by suitable scanning apparatus disposed in or operable in connection with a commercially available copying, or printing device, as will be identified below. The electronically recorded information may be further processed using typically, commercially available communications equipment, such as the facsimile system in common use at the present time, and various and sundry other forms of communication.

In further utilization of the principles of my invention, the permanently mounted records in the form of indicia disposed upon the flexible transparent plastic tape may be utilized in conjunction with an ordinary copying machine which may then reproduce the images upon suitable records retaining media for use in processing the information and/or to be disposed in files or the like for future reference.

A further embodiment of the invention facilitates coating the digital extremities of an individual with a uniform coating of ink, powder or the like by providing a rotary turntable that is disposed on the surface of a workbench upon which a holding means or an adhesive recording strip is provided to accept the images of the digital extremeties of the individual after they have been suitably coated with the powder or ink. The digits of the individual are rolled as they are placed on the peripheral top surface of the table and in doing so, the turntable rotates as the digit is rolled so a uniform coating of the ink or powder is deposited upon the digital extremity.

These and other objects of my invention may become apparent from a consideration of the appended specification, claims and drawings which:

FIG. 1 is a top perspective view of apparatus for effectuating the principles of my invention;

FIG. 1 is an enlarged front elevational view of a print recording staion as illustrated on FIG. 1;

FIG. 10 and FIG. 10A are front and side views of an opaque print card having a plurality of print images disposed thereon;

FIG. 11 and FIG. 11A illustrate the rear and one edge of a transparent print card;

FIG. 12 and FIG. 12A represent the front and one edge of a transparent print card;

FIG. 14 illustrates the front surface of the transparent print card depicted in FIG. 12 having the images of FIG. 8 diposed thereon as viewed from the front side;

DETAILED DESCRIPTION OF THE INVENTION

Figure 1A:
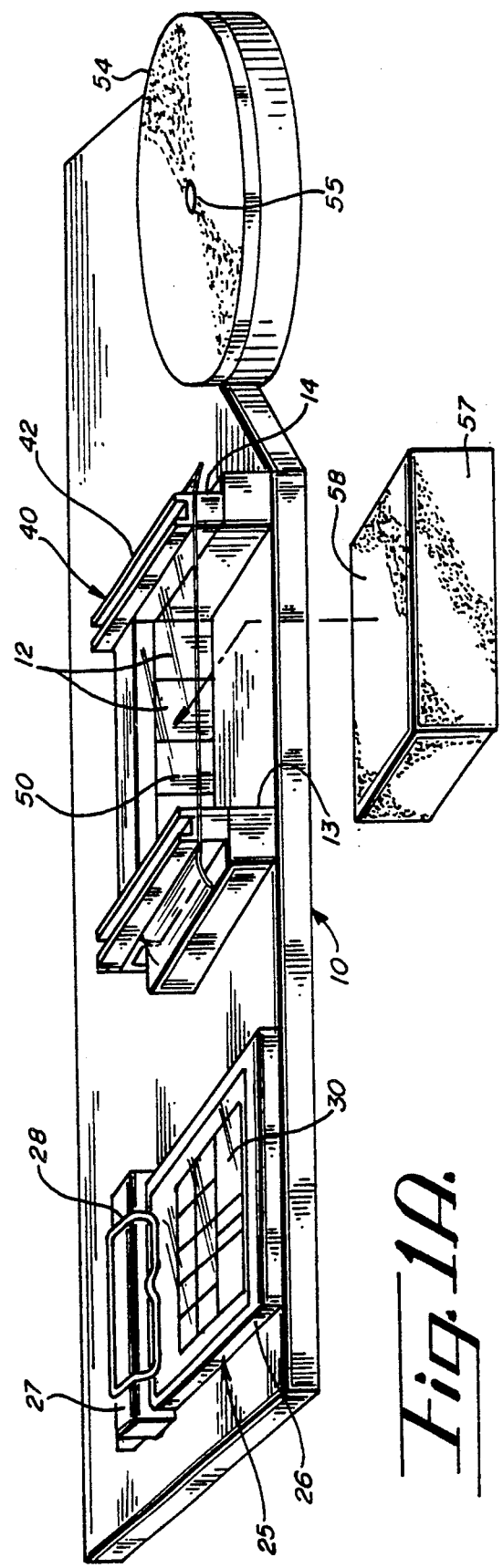
FIG. 1A is a top perspective view of a further embodiment of the apparatus illustrated in FIG. 1.

Referring now to the drawings in which like elements are identified by like reference characters, FIGS. 1-4 illustrate apparatus whicy may be used to carry out the method of my invention which includes a base 10, which may be a tabletop suported by appropriate structure (not shown) at a convenient adjustable height for use by an operator in obtaining the images of the ends of the digits of an individual. Suitably disposed on table 10 are an ink, or powder base 20 which includes a frame 21, for purposes to be described below; a print form holder 25, which includes a base 26 having a top 27 and a spring holder 28, for engaging the top end of a print slide card 30, shown in the form of a transparent square of stable plastic material, on top 27 of base 26. A U-shaped frame 40 is shown comprised of a pair of side arms 41 and 42 disposed in spaced apart parallel relationship and mounted at one end on member 43 which extends perpendicularly therebetween and, as may be seen in FIGS. 3 and 4, frame 40 may be disposed on top of and adjacent to a notch 11 in table 10 or on top of and over base 26 on print form holder 25, for purposes to be described below. Disposed on top of and adjacent to the edges of notch 11 are print frame base members 13 and 14 which support frame 40 and which are provided with stop members 15 and 16 adapted to engage and retain the rear portion of rear member 43 of print frame 40. A plurality of suitable indicia, 12, are disposed on or about frames 13 and 14 and on rear member 43 on frame 40 for guiding the operators in placing the images of the digital extremities of an individual at the appropriate, desired locations on an image recording tape 50, shown disposed across sides 41 and 42 on frame 40 and having an adhesive major surface which is positioned to receive a dusted, or inked digital extremity of an individual when frame 40 is disposed on top of supports 13 and 14.

Figure 3:
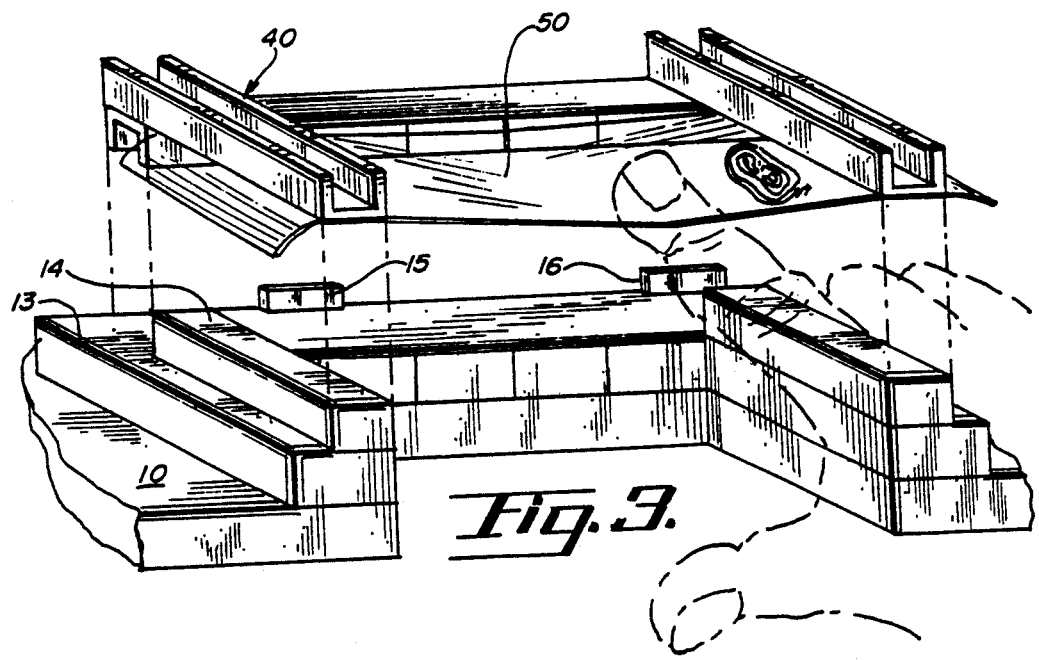
FIG. 3 is an enlarged perspective view of the print recording station of FIG. 2 illustrating the manner in which the apparatus is utilized to perform the principles of my invention.
Figure 4:
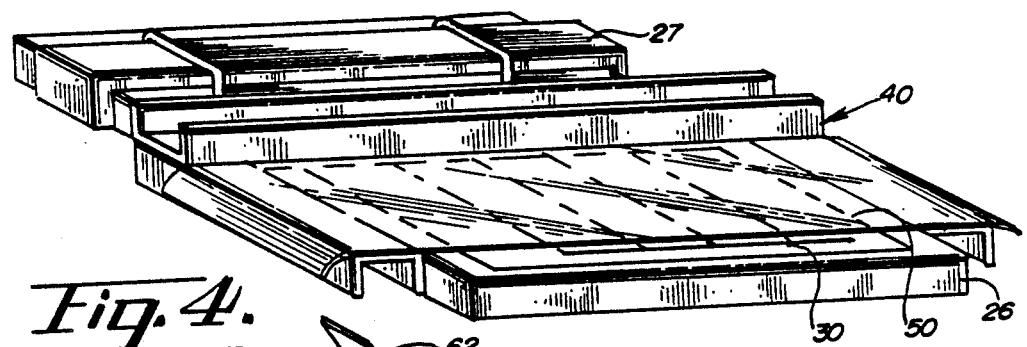
FIG. 4 is an enlarged perspective view of a further portion of the apparatus shown in FIG. 1.

It may be noted that frame 40 is in an inverted position in FIG. 4, from that shown in FIG. 3, to illustrate that the recording media, the adhesive material on the surface of tape 50 is first disposed upwardly to receive the surface of the remotely disposed digit, the image of which is to be recorded, and then is disposed with the adhesive side opening downwardly, as in FIG. 4, for affixation to a transparent print slide card or carrier 30 at predetermined locations as guided by the indicia disposed on the top 27 of print form holder 25 so that the digits may be disposed on print slide card 30 at the locations that will correspond to the transparent record cards 32 or opaque record card 65, each having appropriately disposed indicia to identify the images transferred thereto.

Referring to FIG. 1A, the modifications that are illustrated may be apparent from a comparison of FIGS. 1 and 1A and will show that notch 11 is no longer present and that base 10 provides a solid surface adjacent to and underneath frame 40 and print frame base members 13 and 14 and ink base 20 has been replaced by turntable 54 that is rotatable about a pivot 55 on the surface of base table 10 and adjacent to the right end. A foam block 57, which may conveniently be disposed within a suitable plastic envelope 58 may be disposed within print base members 13 and 14 and on top of base table 10 to provide a resilient backing for print recording strip tape 50 as digital impressions are recorded thereon.

Figure 5:
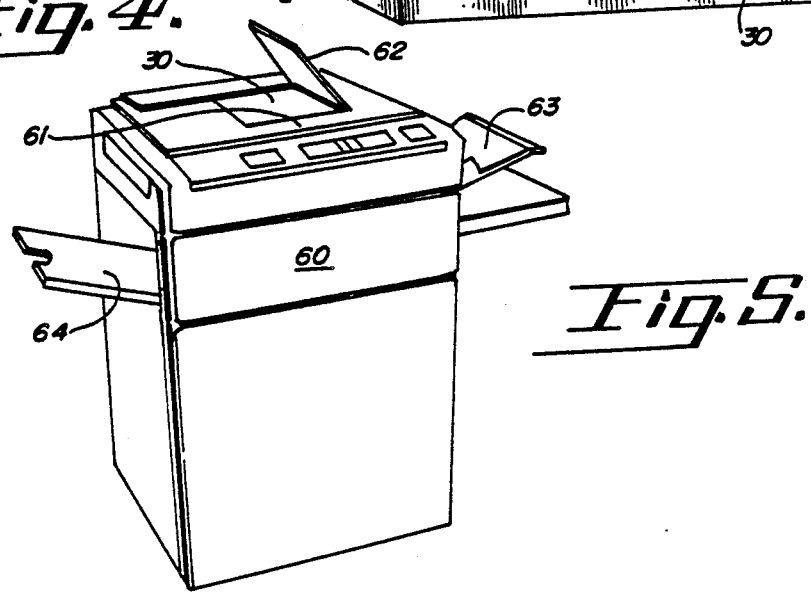
FIG. 5 is a perspective sketch of a representative commercial copying machine that has been suitably modified to effectuate the principles and method of my invention.

FIG. 5 illustrates a copier 60 having a top opening 61 dimensioned to receive a standard 8 by 8 sized media utilized in connection with fingerprint technology, a cover 62, a supply of media to which images are to be transferred, 63, an exiting ramp 64 and a plurality of unidentified controls for the operation of the copying machine. A suitable copying machine for the purposes of practicing my invention may be the Panasonic Model FP-1530 or the Harris/3M Model P 1100-0163, 6215 copying machine.

Figure 6:
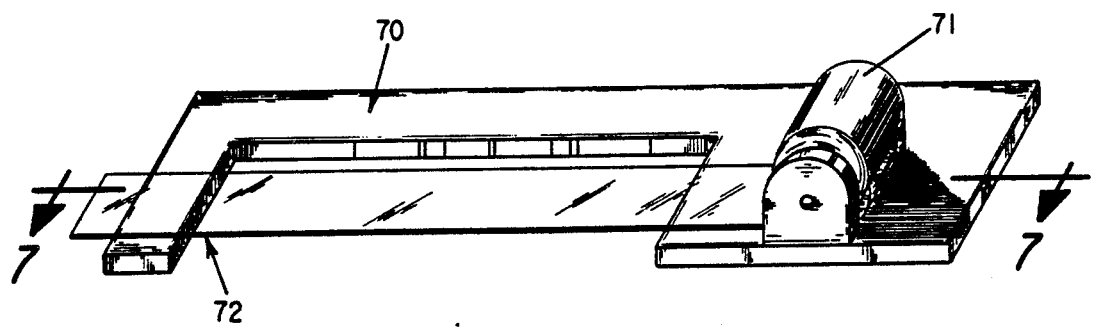
FIG. 6 is a fragmentary view illustrating a further embodiment of apparatus which may be used in conjunction with effectuating the principles of my invention.
Figure 7:
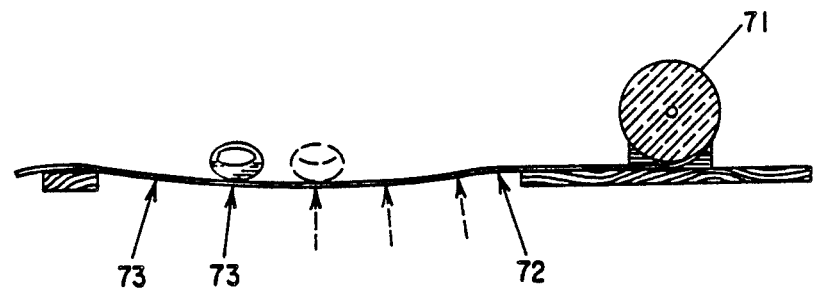
FIG. 7 is a sectional view taken along section line 7—7 on FIG. 6.

FIGS. 6 and 7 illustrate a portable image recording print frame 70, having a notch 72 and a supply of image recording tape, indicated by reference character 71, that may be disposed across notch 72 in a manner similar to that shown in connection with FIGS. 1, 2, 3 and 4. Frame 70 is intended to be utilized under conditions wherein the individual from whom the images of the remote digital extremities are to be recorded is either uncooperative or unable to move, and therefore, the frame 70 may be moved relative the digit being recorded and a completely satisfactory set of images obtained.

Figures 8, 8A:
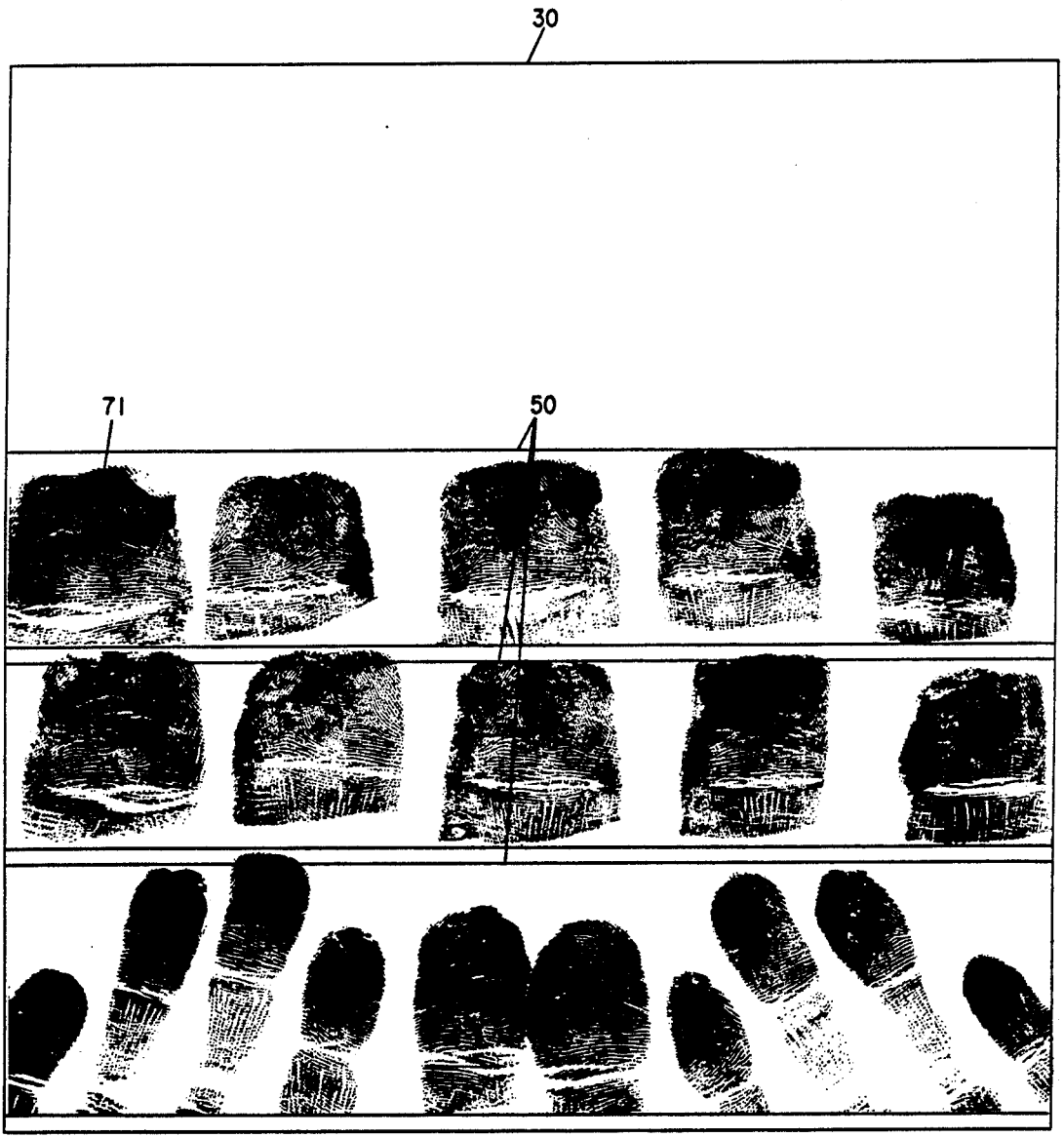
FIG. 8 and FIG. 9 are front and back views, respectively, of a records print slide.
FIG. 8A and FIG. 9A are edge views of FIGS. 8 and 9.
Figures 9, 9A:
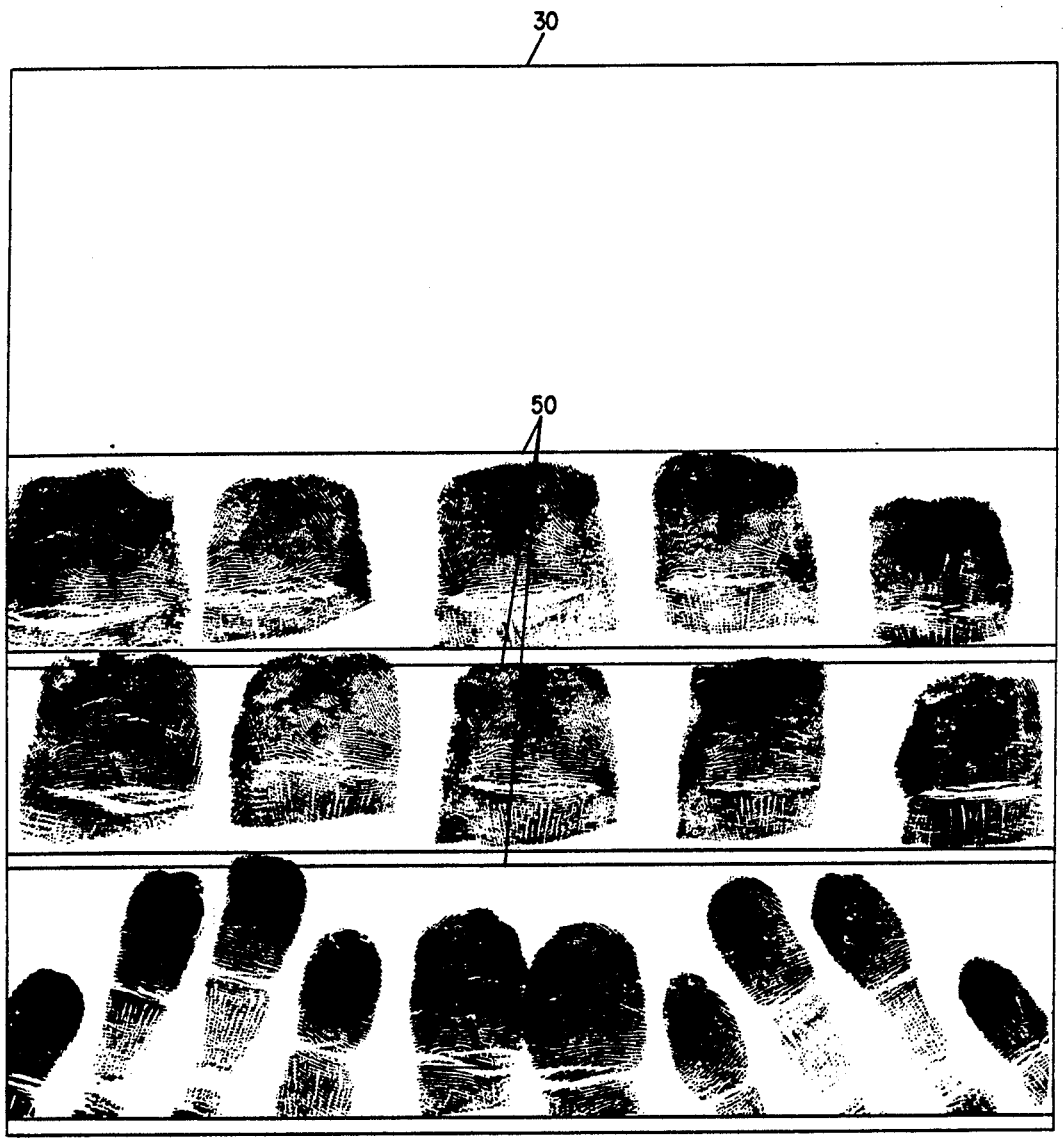

In FIGS. 8 and 9, the front and rear surfaces of a print slide card 30, comprised of a sheet of suitable stable, transparent plastic material is illustrated as having a plurality of image recording strips of tape 50 disposed on the front surface of FIG. 8 and may thus be sen, in reverse for and through the rear surface shown on FIG. 9.

Figure 10:
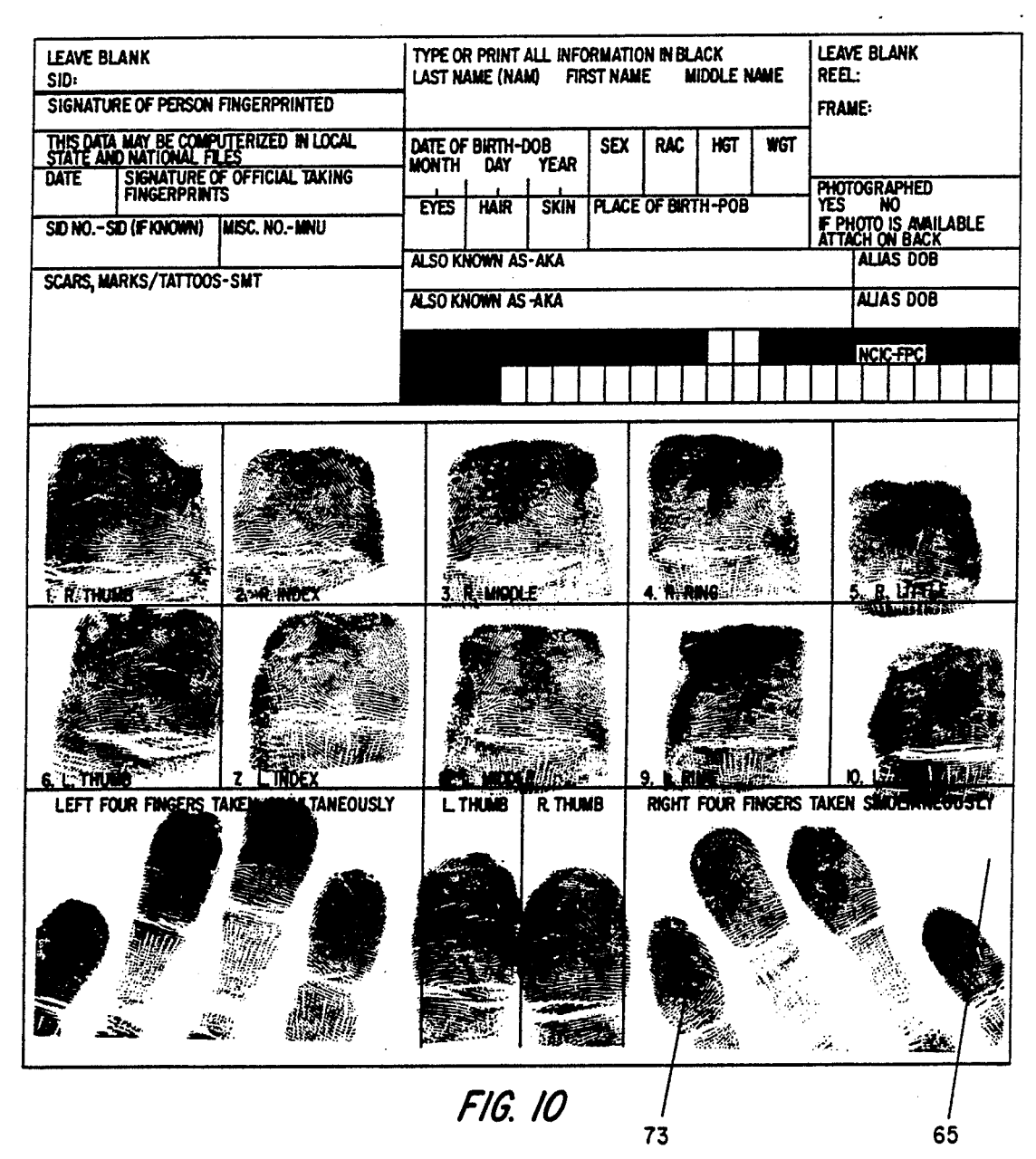
Figure 10A:
Figure 15A:
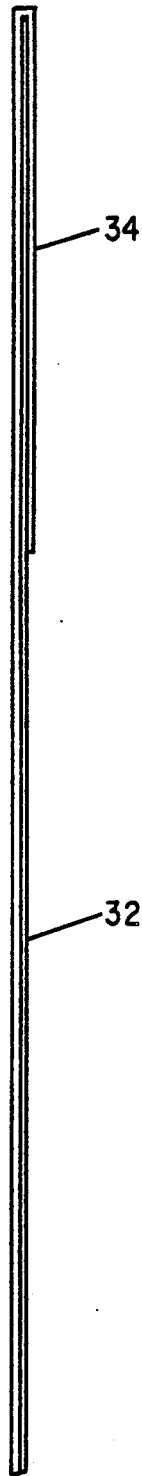
FIG. 15 and FIG. 15A illustrate the front and edge view of one records retention device.
Figure 16A:
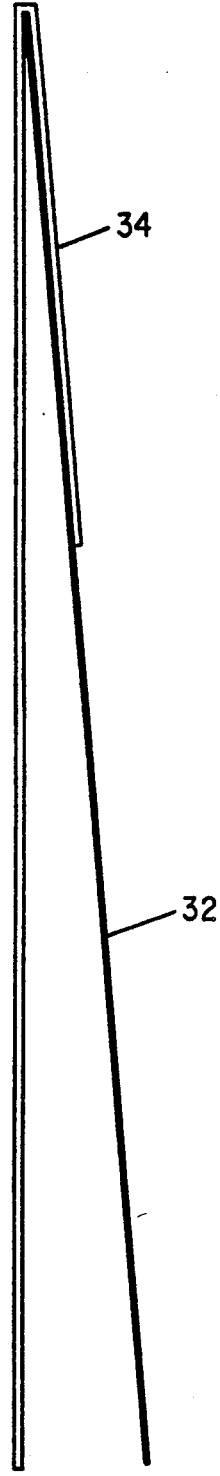
FIG. 16 and FIG. 16A represent a further embodiment of a records retention device according to the principles of the invention.

FIG. 10 and 10A show an opaque card 65 having suitable indicia preprinted thereon and upon which the images of the records contained on slide card 30 have been transferred through the use of copier 60, or the like apparatus.

Figure 13:
FIG. 13 illustrates a print record, as illustrated in FIG. 8, transferred to the rear surface of the transparent print card of FIG. 11.
Figure 14:
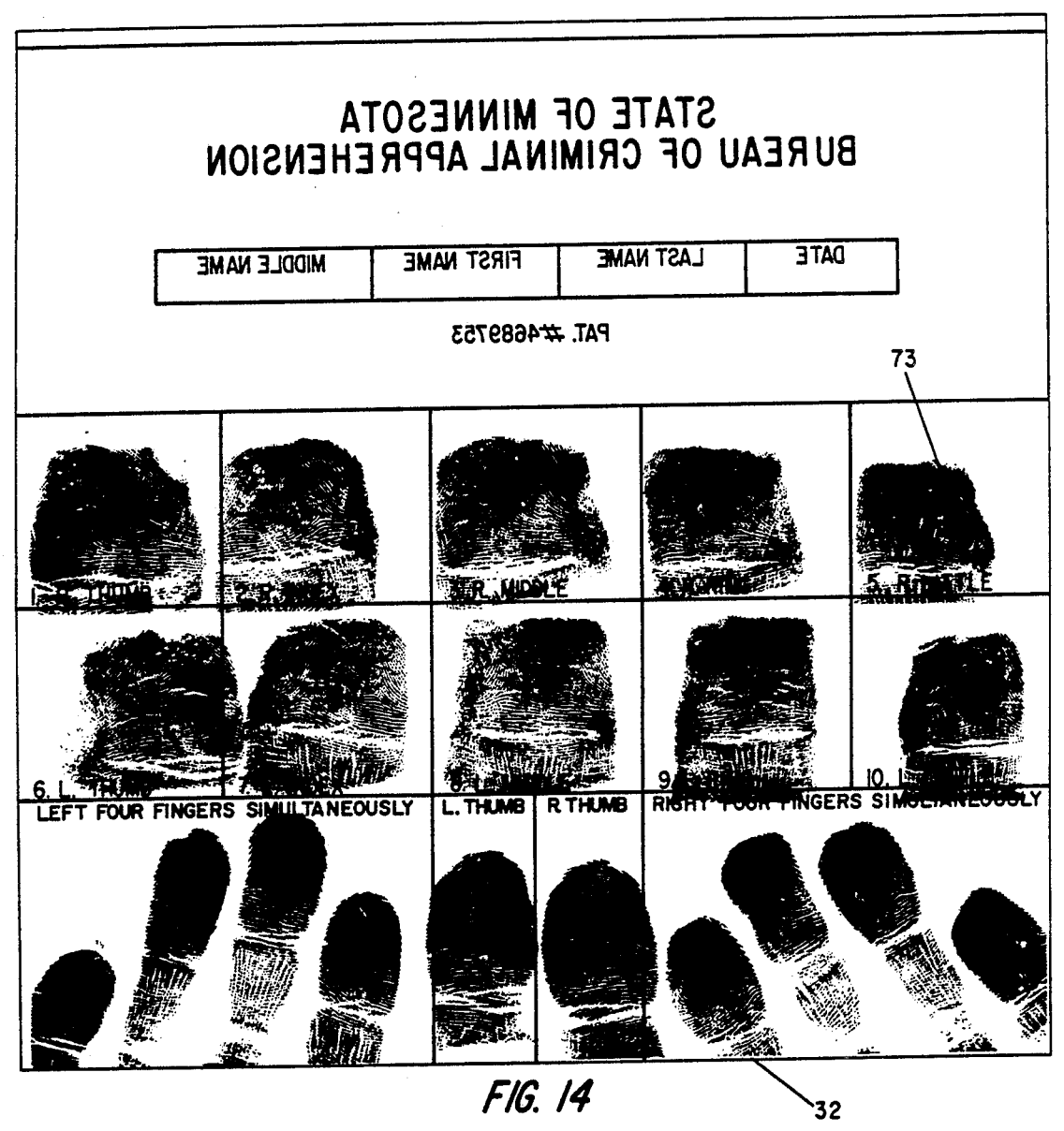

Referring to FIGS. 11, 12, 13 and 14, a stable, transparent, record card 32 is shown on a rear view FIG. 11, having suitable indicia printed thereon, a front view FIG. 12, having suitable indicia printed thereon, and corresponding views of FIGS. 13 and 14 having images, as obtained from the record of card 30 of FIGS. 8 and 9 disposed at the proper locations for identification processing purposes.

Figure 15:
Figure 16:

Transparent record card 32 may be disposed in a completely sealed card and contained within and upon base 34, as in FIG. 15, through the use of suitable adhesive material and a further record, known as a flyer record, is shown in FIG. 16 in which only the upper portion of transparent record card 32 is attached to the underside of the top portion of base card 34 so that the materials contained on transparent record card 32 may be viewed from the front or the back to obtain the advantage of viewing a print image from one or two directions.

OPERATION

Referring to the drawings and the description set forth above, when it is desired to record the images of the digits of an individual, as for example, fingerprints, a strip of tape 50 is disposed across the side arms of frame 40 and frame 40 is oriented so that adhesive mterial on one major surface of tape 50 is oriented upwardly so that it may be engaged, for example, by the finger of an individual as illustrated in phantom outline on FIG. 3 of the drawings and it will be seen that tape 50 may deflect downwardly as pressure is applied from a digit, the image of which is to be recorded thereon, is pressed downwardly and, preferrably, rolled from side to side or from front to back, depending on the nature of the images to be recorded.

While an adhesive coated tape 50 may be sufficient to record visible images, it may be necessary to coat the digits of an individual with a visible medium, such as powder or ink, either of which may be distributed upon base 20, within the confines of frame 21, or on the top surface of turntable 54 in FIG. 1A, so that a digit may be first pressed upon the surface of base 20 prior to application to tape 50 in a location which may be determined by the indicia, 12, disposed on print frame 40 and/or print frame base such as 13 and 14. After the desired images have been created upon the adhesive surface on tape 50, frame 40 may be lifted upwardly, turned over and disposed over a transparent print card 30 disposed on the top surface of form holder 25 and held in place by spring clip 28, generally as illustrated in FIG. 4 whereat the position of the now downwardly facing adhesive coating on tape 50 may be disposed at suitable locations as determined by the position of suitable indicia present upon the top surface of base 26. Disposing the desired strips of tape 50 upon the surface of print card 30 creates a permanent record that may be utilized to create other records or for immediate further processing as may be desired.

It is also possible to retain the tape strip 50 on frame 40 or to utilize the strip in the embodiment of FIGS. 6 and 7, in conjunction with a high resolution electronic scanning means (not shown) which may readily convert the images on tapes 50 or 71 to electronic signals which may be stored in a suitable memory and/or transmitted to remote locations.

As may now be appreciated, the embodiment of FIGS. 6 and 7 provides a frame 70 that may be easily transported and moved to accommodate unconscious, handicapped or uncooperative individuals who present specific problems to obtaining records of the images of the digital extremities.

It may now be clear to those skilled in the art that the images recorded may be disposed on an opaque card 65 as on FIGS. 10 and 10A through the use of suitable printing or copying machine, or may be further reproduced on a surface of transparent record card 32, which may then be used by itself or as incorporated in or associated with records retention bases 34 as illustrated on FIGS. 15 and 15A or FIGS. 16 and 16A.

It may also be seen that the print images are captured on a adhesive coating on one side of a clear plastic film strip. Whether or not the digital extremity, the image of which is to be recorded, is coated with ink or powder or the like, a recognizable, usable image is recorded without distortions, smudges or smears. The image may then be transferred, as printing or electronic scanning, to suitable recording media.

I claim:

1. Fingerprinting apparatus comprising:
    (a) dispensing means for dispensing a transparent, flexible film media having at least one surface containing a layer of adhesive;
    (b) coating means containing an opaque material for coating the distal digits of a plurality of fingers of a subject brought into contact with the material and wherein said material bonds to the adhesive;
    (c) frame means mounted to a support surface adjacent the dispensing means and coating means and including first and second arm portions for supporting said film media in suspension therebetween and above said support surface and including indicia means for individually aligning coated fingers to the adhesive layer of said film media as the fingers are brought into contact with the adhesive layer, whereby an opaque image of each finger is obtained at predetermined surface locations of said film media; and
    (d) carrier support means mounted adjacent said frame means for supporting a print carrier to permit the alignment of an imaged adhesive layer to the print carrier prior to bonding the adhesive layer to said print carrier.

2. Apparatus as set forth in claim 1 wherein the opaque material comprises printer's ink.

3. Apparatus as set forth in claim 1 wherein the opaque material comprises a fine graphite powder.

4. Apparatus as set forth in claim 1 wherein a deformable pad is mounted to the support surface in the space between the first and second arm portions and beneath the film media such that said film 5. Apparatus as set forth in claim 1 wherein said coating means rotates upon bringing a finger into contact contact with the coating material for evenly coating the finger with said media as the finger is rotated with respect thereto.

6. Apparatus as set forth in claim 1 wherein said frame means includes means removably mounting to the first and second arm portions for restraining a length of the film media thereto as each finger is brought into contact with teh adhesive layer and for cooperating with the carrier supportmeans to align the iamge containing film media to the print carrier and bond the adhesive layer to the print carrier.

7. Apparatus as set forth in claim 1 wherien said print carrier comprises a rigid substrate capable of permanent storage.

8. Apparatus as set forth in claim 7 wherein said print carrier comprises an opaque card including a plurality of scribed indicia whereat fingerprint images on the film media are alignable and data identifying the subject and fingers.

9. Apparatus as set forth in claim 7 wherein said print carrier comprises a transparent substrate and includes a plurality of scribed indicia whereat fingerprint images on the film media are alignable and data identifying the subject and fingers.

10. Apparatus as set forth in claim 1 wherein the carrier support means is mounted to said support surface and includes means for restraining the print carrier thereto and wherein said frame means includes means removably mounting to the first and second arm portions for restraining a length of film media thereto as each finger is brought into contact with the adhesive layer and for cooperating with the carrier support means to align the film media to the print carrier and bond the adhesive layer to the print carrier.

11. Apparatus as set forth in claim 1 wherein the dispensing means comprises means for dispensing cut lengths of the film media from a roll in lengths sufficient to span said first and second rail portions.

12. Fingerprinting apparatus comprising:
    (a) a support base including indicia means for aligning a finger therewith;
    (b) dispensing means secured to said base for dispensing predetermined lengths of a transparent, flexible film media having at least one surface containing a layer of adhesive;
    (c) coating means secured to said support base containing an opaque, high contrast material for coating the distal digits of a plurality of fingers and wherein said material bonds to the adhesive layer of the film media;

(d) frame means secured to said support base comprising a U-shaped framework having first and second arm portions mounted to restrain a length of said film media therebetween in suspension above said support base for individually aligning the coated fingers of a subject to the adhesive layer of said film media as the fingers are brought into contact with the adhesive layer, whereby an opaque image of each finger is obtained at predetermined surface locations of said film media;

(e) carrier support means secured to said base for supporting a print carrier containing scribed indicia whereat fingerprint images on the film media are alignable and data identifying a subject; and (f) wherein a portion of said frame means which supports the film media is removable and alignable with the carrier support means for presenting the adhesive layer to effect the bonding of the adhesive layer and finger images in predetermined orientation to said print carrier.

13. Apparatus as set forth in claim 12 wherein said coating means rotates upon contact with a finger for evenly coating the finger with said media as the finger is rotated with respect thereto.

14. Apparatus as set forth in claim 12 wherein a deformable pad mounts between said first and second arm portions beneath the film media such that said film media contacts said pad as individual fingers contact the film media.

* * * * *